(12) United States Patent
Danehy et al.

(10) Patent No.: US 7,675,619 B2
(45) Date of Patent: Mar. 9, 2010

(54) MICRO-LIDAR VELOCITY, TEMPERATURE, DENSITY, CONCENTRATION SENSOR

(75) Inventors: Paul M. Danehy, Newport News, VA (US); Adrian A. Dorrington, Hamilton (NZ)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 165 days.

(21) Appl. No.: 12/129,967

(22) Filed: May 30, 2008

(65) Prior Publication Data

US 2009/0122314 A1    May 14, 2009

Related U.S. Application Data

(60) Provisional application No. 60/987,794, filed on Nov. 14, 2007.

(51) Int. Cl.
*G01N 21/00* (2006.01)
(52) U.S. Cl. ........................... 356/337; 356/342
(58) Field of Classification Search .......... 356/335–344
See application file for complete search history.

(56) References Cited

U.S. PATENT DOCUMENTS

| | | |
|---|---|---|
| 3,646,749 A | 3/1972 | Clough et al. |
| 4,707,134 A * | 11/1987 | McLachlan et al. ......... 356/342 |
| 4,788,084 A | 11/1988 | Morin |
| 5,221,956 A | 6/1993 | Patterson et al. |
| 5,317,376 A | 5/1994 | Amzajerdian et al. |
| 5,394,238 A | 2/1995 | Mocker et al. |
| 5,424,824 A | 6/1995 | Daiber et al. |
| 5,594,543 A | 1/1997 | Groot et al. |
| 5,610,705 A | 3/1997 | Brosnan et al. |
| 5,793,478 A | 8/1998 | Radar et al. |
| 5,872,621 A | 2/1999 | Wilkerson et al. |
| 5,967,400 A | 10/1999 | Bell et al. |
| 6,233,047 B1 * | 5/2001 | Jung et al. .................... 356/73 |
| 6,320,651 B1 | 11/2001 | Manhart et al. |
| 6,433,861 B1 | 8/2002 | Nagele et al. |
| 6,469,778 B2 | 10/2002 | Asaka et al. |
| 6,535,276 B2 | 3/2003 | Dubois |
| 6,571,118 B1 * | 5/2003 | Utzinger et al. ............. 600/476 |
| 6,646,725 B1 | 11/2003 | Eichinger et al. |
| 6,885,438 B2 | 4/2005 | Deines |
| 6,894,768 B2 * | 5/2005 | Caldwell et al. .............. 356/28 |
| 7,495,774 B2 * | 2/2009 | Hays et al. .................. 356/519 |
| 2004/0142484 A1 * | 7/2004 | Berlin et al. ................ 436/171 |
| 2005/0062955 A1 | 3/2005 | Deines |

* cited by examiner

*Primary Examiner*—Gregory J Toatley, Jr.
*Assistant Examiner*—Jarreas C Underwood
(74) *Attorney, Agent, or Firm*—Helen M. Galus

(57) ABSTRACT

A light scatter sensor includes a sensor body in which are positioned a plurality of optical fibers. The sensor body includes a surface, in one end of each of the optical fibers terminates at the surface of the sensor body. One of the optical fibers is an illumination fiber for emitting light. A plurality of second optical fibers are collection fibers for collecting scattered light signals. A light sensor processor is connected to the collection fibers to detect the scattered light signals.

6 Claims, 4 Drawing Sheets

MICRO-LIDAR VELOCITY, TEMPERATURE, DENSITY, CONCENTRATION SENSOR

ORIGIN OF THE INVENTION

This invention was made in part by an employee of the United States Government and may be manufactured and used by or for the Government of the United States of America for governmental purposes without the payment of any royalties thereon or therefor. Pursuant to 35 U.S.C. §119, the benefit of priority from provisional application 60/987,794, with a filing date of Nov. 14, 2007, is claimed for this non-provisional application.

FIELD OF THE INVENTION

The present invention is directed to a light scattering sensor. Specifically, the small sensor has a plurality of optical fibers that terminate on the surface of the sensor for N emitting light and collecting scattered or absorbed and reemitted light.

BACKGROUND

Many types of detection and ranging sensors are known and widely used in practice. These sensors include RADAR and LIDAR systems generally. Traditionally, these types of sensors are relatively large in size and limited in application.

In one example, LIDAR is used to detect the velocity of an object. The velocity can be measured, because the light scattered back toward the source is Doppler shifted by a moving object—the larger the velocity, the larger the Doppler shift. However, conventional LIDAR tends to use a small angle between the light source and the detector, meaning the system is only sensitive to the component of velocity approximately in the direction of the laser light propagation. For instance, detection of the speed of a distant object in a direction other than that of the sensing beam propagation using a conventional LIDAR is limited. Therefore, there is a need for a sensor able to detect multiple components of velocity of a target object or gas; in fact measurements of multiple components of velocity are required at multiple small, known, spatial locations above a surface to determine a gas boundary layer profile, for example. In addition to velocity, other parameters such as temperature, density and gas composition are desired to be measured.

SUMMARY

Accordingly, it is an object of the present invention to overcome the foregoing limitations. The present invention provides a micro-LIDAR sensor that is structurally small and that is adapted to collect scattered light from multiple directions in order to provide more information regarding the target of the emitted light.

In one example, a light scatter sensor comprises a sensor body in which are positioned a plurality of optical fibers, wherein the sensor body includes a surface and one end of each of the optical fibers terminates at the surface of the sensor body. A first optical fiber of the plurality of optical fibers is an illumination fiber for emitting light. A plurality of second optical fibers of the plurality of optical fibers are collection fibers for collecting scattered light signals. The sensor further comprises a light signal processor connected to the plurality of collection fibers and adapted to detect the scattered light signals collected by the collection fibers. A field of view of the emitted light intersects with a field of view of a first collection fiber, a second collection fiber, and a third collection fiber to form a measurement volume defined by the intersection of the three collection fiber fields of view in the emitted light field of view. Alternatively, a plurality of measurement volumes may be detected by a plurality of sets of at least three (3) collection fibers. The ends of the collection fibers that terminate at the surface of the sensor body may each comprise a lens. The first, second and third collection fibers may be positioned substantially equidistantly around an imaginary circle defined by the ends of the three (3) collection fibers, and the end of the illumination fiber is positioned substantially in the center of the imaginary circle. In another example there is a plurality of sets of collection fibers. Each set of at least three (3) collection fibers is positioned substantially equidistantly around the imaginary circle defined by the ends of the three (3) collection fibers, and the end of the illumination fiber is positioned substantially in the center of the imaginary circle. In this example, each set of collection fibers defines a different sized circle from the other sets of collection fibers, therefore sensing a different measurement point above the surface.

DETAILED DESCRIPTION

Sensors described herein are scattered light sensors adapted to be effective at relatively short operation distances between measurement volumes and collection optics. In one example, the operation distance is between about two hundred micrometers and five centimeters, or alternatively, between about one millimeter and one centimeter. In one example of the present sensor, the sensor is incorporated into a Rayleigh scatter velocimeter. Commercial velocimeters rely on scattering from particle-seeded flows and operate primarily in the Mie scattering regime, because the Rayleigh scattering efficiency is comparably very low. Therefore, current methods of implementing Rayleigh scattering require high levels of laser illumination, large collection optics, and sensitive detectors.

The present sensor is described in the following example in a Rayleigh scatter velocimeter. There are other applications for the sensor including, but not limited to, other applications described herein.

Figure 1:
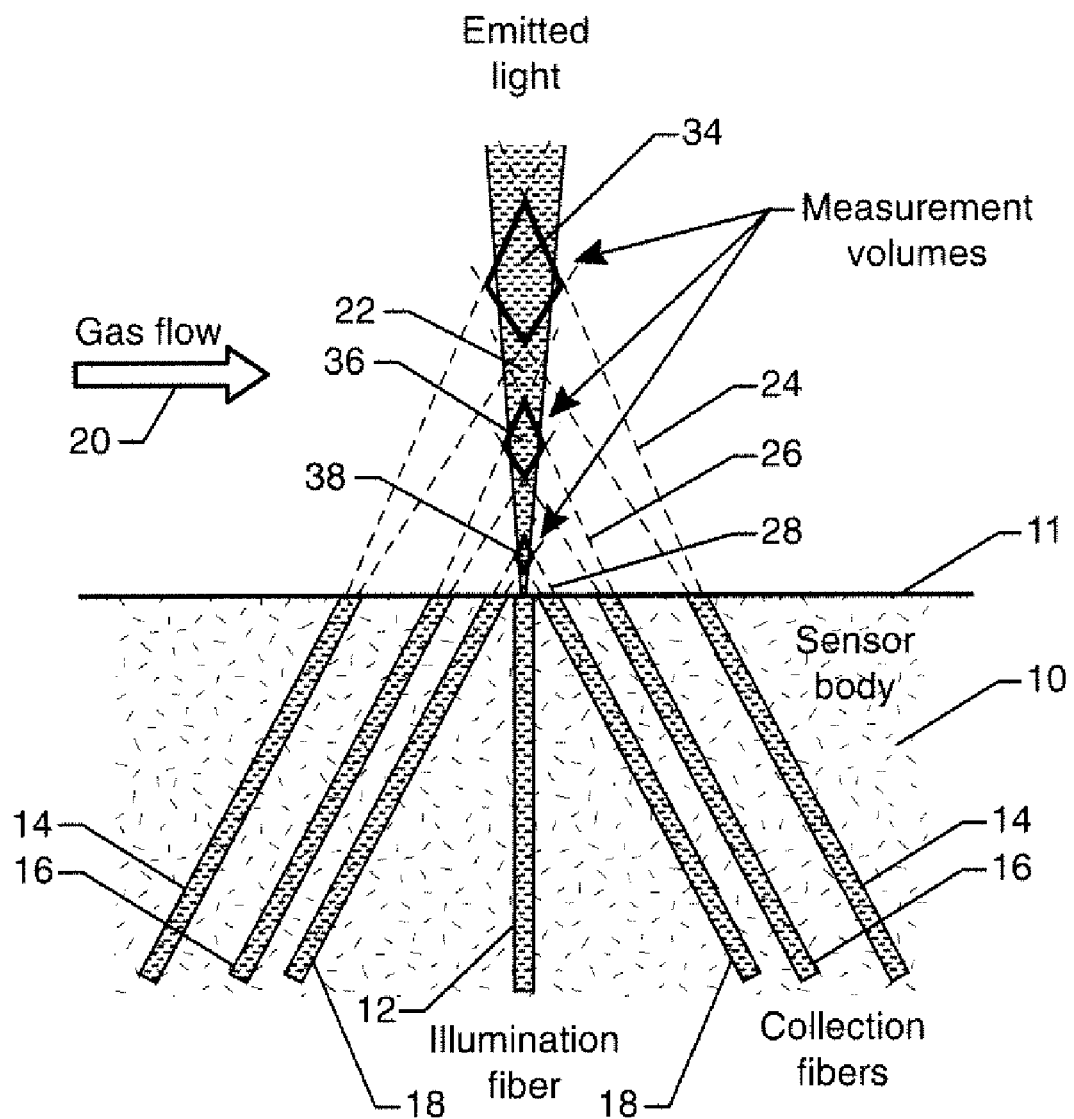
FIG. 1 is a side view of an example of a sensor configuration in accordance with the sensor described herein.
Figure 2:
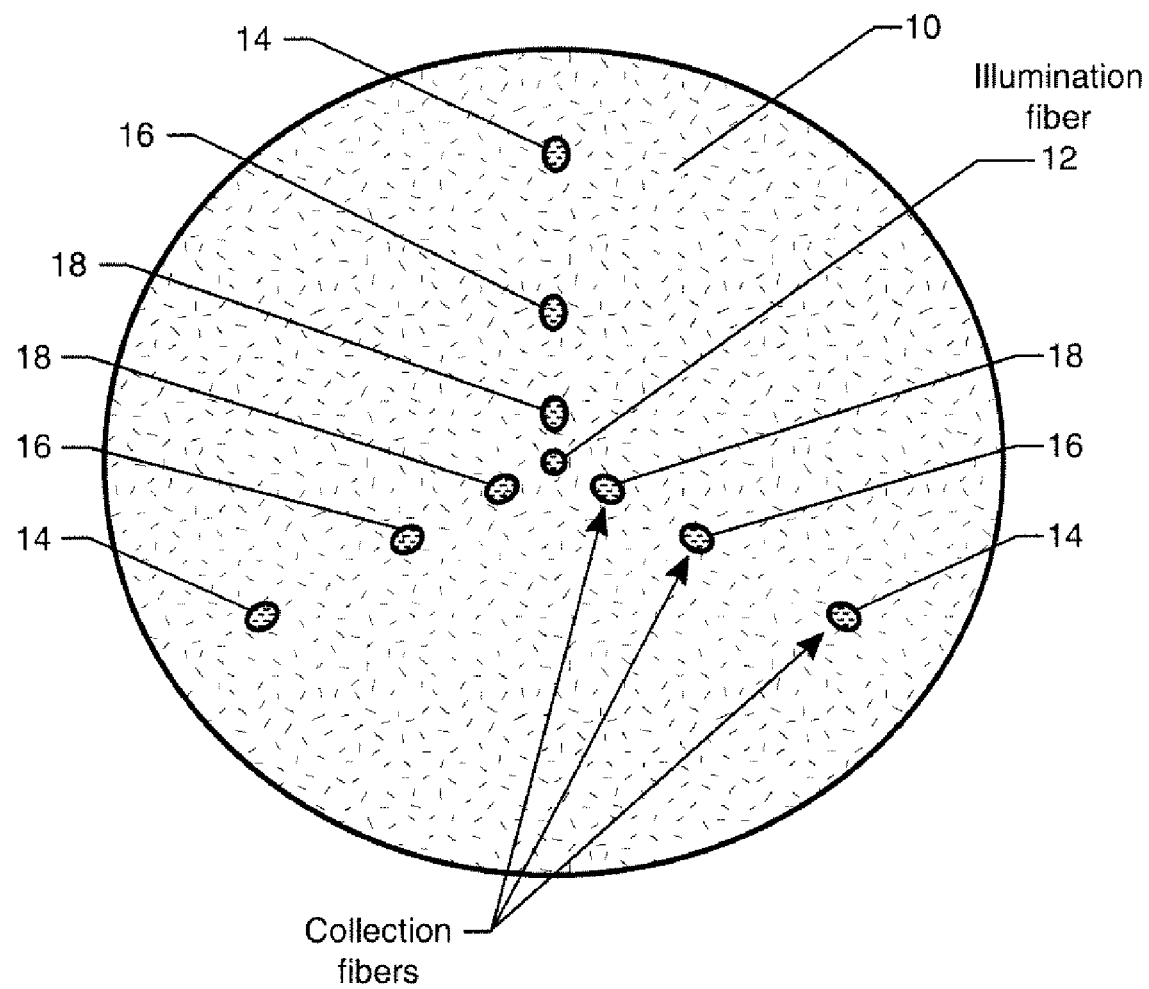
FIG. 2 is a top view of an example of a sensor as described herein.

FIGS. 1 and 2 illustrate the proposed sensor configuration 10. Illumination light 22 is provided by the illumination fiber 12 located in the center of the sensor head surface 11. Several other sets of optical collection fibers 14, 16 and 18 are used to collect Doppler shifted light and deliver it to a light signal processor. Measurement volumes 34, 36 and 38, in which the flow velocity can be determined, are defined by the intersection of the field of view of both the illumination 22 and collection optics 24, 26, and 28. The ability to simultaneously obtain velocity measurement in several measurement volumes 34, 36 and 38 aligned vertically above the illuminating fiber 12 (in the "z" direction), as indicated in FIG. 1, is provided by the geometry of multiple sets of collection fibers 14, 16 and 18. In principal, more measurement volumes can be added by using more fibers. Furthermore, three-components of the flow velocity can be measured by the positioning of three separate collection fibers, arranged in a circular pattern, for each measurement volume. In each case, the velocity component measured is the component in the angle that bisects the illuminating fiber and the collection fiber. Once three independent velocity components are measured, a coordinate transformation can be used to determine the velocity components in the familiar "x, y, z" directions.

In one example, existing fiber-optic and graded-index lens technology is assembled into a custom sensor head. The head could be as large as several centimeters in diameter, or as small as several millimeters in diameter, using traditional multi-mode fibers of 125 micro-meter cladding diameter fiber. Such an example, depending on the configuration, could perform measurements in the range of several centimeters to 200 micrometers off the surface.

In one example fabrication method, the fiber ends or graded index lens ends are embedded into a sensor head. Because it is important to not perturb the flow, the sensor head surface is flat and free from obstructions, the fiber or lens elements, which are mounted on an angle, must be positioned slightly below the surface of the sensor head. In such a case, the positioning angle of the collection fiber or lens must be adjusted to compensate for surface refraction, and the sensor head surface must be polished for an optical flat finish.

In a further example fabrication method, the fiber or lens elements are mounted such that they protrude above the sensor surface, and are subsequently polished flat. In this example, the sensor head forms only a mechanical support for the illumination and collection optics, and is not integral in the optical path. Refraction effects must still be considered in the positioning of the collection fibers or lenses. This example is shown in FIG. 1.

Light sources could be monochromatic fixed-frequency lasers for velocity, temperature, density and frequency doubled dye lasers or Optical Parametric Oscillators (OPO) for species measurements. It is possible to put about 20 mJ/pulse of Nd:YAG light into a fiber and this is enough to make measurements of velocity, density and temperature. These lasers are typically 10 Hz but such lasers are available at up to MHz rates, allowing measurements at high rates to resolve the time-domain flow fluctuations. Also, long pulse or continuous wave laser sources (such as Argon Ion or Nd:YAG) could be used. It is possible that smaller laser sources could be used, such as diode lasers and other technologies but these are generally lower power.

The illumination and collection fibers and lenses are arranged such that the free-space optical paths overlap forming an intersection volume in which measurements are performed. For better discrimination between velocity components, larger angles between all collection fibers is preferable though larger angles result in an overall larger device size. Also the largest angle is theoretically limited by total internal reflection, which is about 45 degrees, depending on the index of refraction of the medium. Fibers at a greater angle will collect no light from above the surface (assuming they are either polished flat to the surface or are looking through a window that is polished flat to the surface). If grooves in the surface or fibers protruding out over the surface can be tolerated, collection angles greater than 45 degrees can be obtained. The collection optics angle and radial distance between the collection optics and illumination optics are determined as a function of velocity measurement precision, measurement volume height above the surface, and refection effects at the sensor head glass/gas boundary. Larger angles typically necessitate a lager sensor head sizes, because the limited bend radius of the fibers necessitates more physical space to arrange the collection fibers in a bundle. Larger measurement column distances off the surface of the sensor head also typically necessitate a larger sensor head, because geometry requires a larger radial distance between the collection optics and illumination optics, while maintaining optimized collection optics angles.

Signal Detection and Processing

Light signal processors are used to extract relevant information from the light signals collected by the collection fibers. Different types of processors may be used depending on the type of light signal that is collected and/or the type information that is desired to be collected by the collection fibers.

For velocity, temperature and density measurement, several satisfactory methods of detecting and processing the light already exist, to be described below. A new concept introduced herein is to detect and process the signals using a wave division multiplexing (or similar) device that would be based on multiple filters that each evaluate fiber outputs signals. Other types of light signal processors that could be used for different applications include those used in the following examples:

Incoherent direct detection (or edge detection) is a common way of determining Doppler shift, particularly with Rayleigh scattered signals that are spectrally-broad when compared with Mie scattered signals. This process involves tuning or choosing a laser wavelength to correspond with the center of a very sharp cut-off optical filter (such as a molecular absorption filter) and passing the collected scattered light through that same filter. Any deviation in the wavelength of the scattered light due to a Doppler shift will cause a corresponding change in amplitude of the filtered light. Processing the ratio of this detected amplitude and the amplitude of the illuminating laser produces an estimation of Doppler shift and hence flow 20 velocity of the air past the sensor. See FIG. 1.

A Fabry Perot etalon can alternately be used to process the signals. The signal is passed through the etalon and imaged onto a CCD camera. The camera observes circular ring-shaped spectra and the position of these spectra on the CCD relate to the Doppler shift. By monitoring the movement of these spectra relative to zero-velocity reference spectra, the velocity can be determined. The shape of the spectrum indicates the temperature and the amplitude of the spectrum indicates the density (if the gas composition is known or can be approximated).

Figure 3:
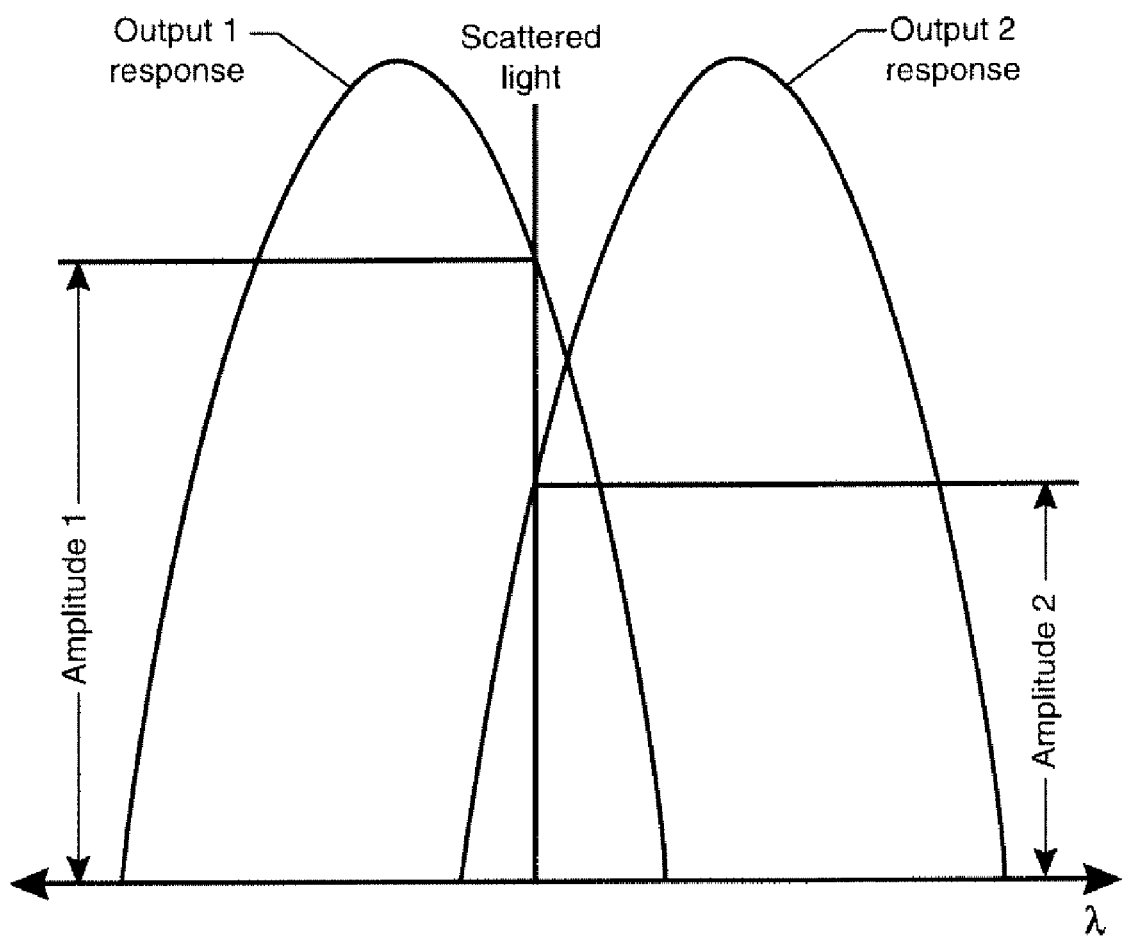
FIG. 3 is a generic spectral response of two (2) outputs of a DWDMD-multiplexer, interleaver, or hyperfine WDM.
Figure 4:
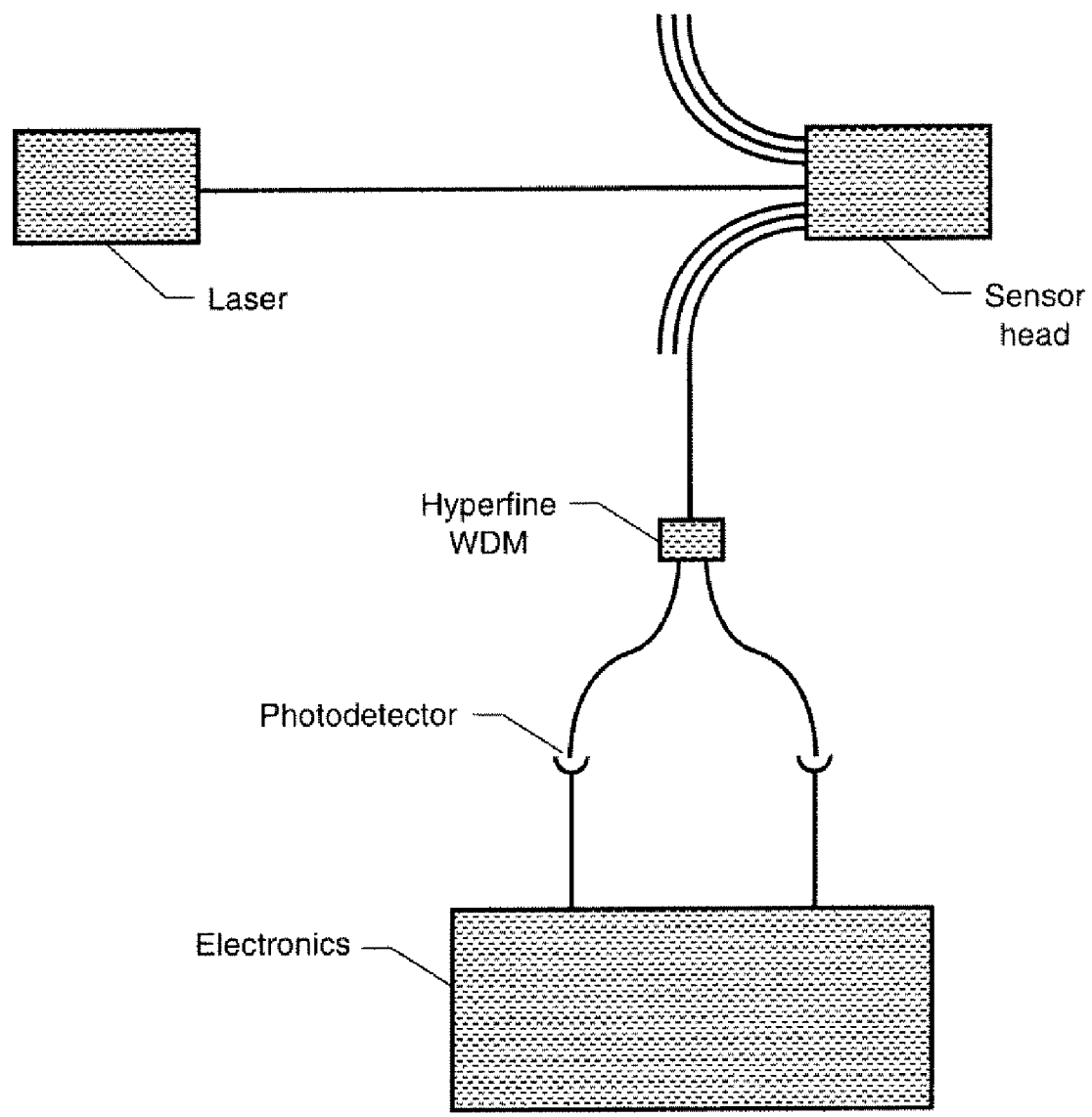
FIG. 4 is a schematic optical configuration showing only one (1) hyperfine WDM on one (1) collection fiber.

Dense Wave Division Multiplexing (DWDM) communications systems commonly use multiplexers, interleavers, and/or hyperfine Wave Division Multiplexing (WDM) devices to combine and separate communications channels that are very closely spaced in wavelength. These devices operate like multiple band-pass filters, one for each fiber output, tuned to the specific wavelength of a communications channel. The response of two of these outputs is illustrated in FIG. 3. Choosing or tuning a laser to correspond with the center overlap of these two outputs will result in an equal signal level from both if the flow velocity is zero so there is no Doppler shift. Any deviation from the center (as illustrated) will produce an increase in one output and a decrease in the other. The ratio of these two outputs can be decoded to determine the Doppler shift, and hence the velocity, as illustrated in FIG. 4. Note that this system does not require the laser output level to be monitored as is required in more traditional direct detection systems, although doing so may provide addition useful information (the gas density). FIG. 4 shows only one Hyperfine WDM on one collection fiber. In practice, this hyperfine device and its associated electronics could be replicated for each collection fiber, or to decrease the cost and size of the system, a time-domain switch could be used to divert light from the different fibers through the WDM sequentially.

The implementation described above uses conventional components. However, there is great potential for development of an integrated sensor. This sensor would use the same or similar technology, but have all the components combined into one miniature Doppler processing package that could fit into a sensor such as that described earlier herein, resulting in an ultra-miniature velocity sensor less that ¼ inch$^3$ in size, which requires only laser light supplied as an input and produces three component velocity outputs from multiple measurement locations. It may also be possible to include the laser source in the sensor head.

Such an integrated sensor would find many applications in a large variety of fields, but one example is active flow control. In this application, the sensor would precede an actuator on an aircraft wing, sense the airflow conditions and feed information to the actuator so it can make appropriate adjustments to improve aerodymanic performance. The sensor could follow an actuator as well: to provide feedback that indicates how the actuator is affecting the flowfield.

In addition to using the proposed, miniaturized optical hardware for Rayleigh scattering velocimetry, the same hardware and setup can be used for several other measurement applications. These shall be described below.

First of all, the same exact sensor could be used without modification to measure the gas density at the same time as velocity. The Rayleigh scattered signal is proportional to the gas density. Thus, a simple calibration procedure could be used to quantitatively relate measured intensity to gas density (assuming that the gas composition is known or could be estimated). If only gas density is required (and not velocity) then a much simpler device could be built: the laser beam would only need to be projected from the surface and viewed by a single fiber or diffractive optical element (DOE) for each measurement location, whereas the velocity sensor requires three fibers/DOE's per measurement location.

Another sensor that could be developed is a particle sensor. If two wavelengths of light are projected from the surface, the intensity of the scattering from these two wavelengths can be used to determine particle size and loading using well-accepted analysis techniques. This could be useful, for example, for measuring and characterizing dust in the Earth or Martian atmosphere either in-flight or on the ground, or for measuring soot particle size in combustion flows.

Still another variation of the sensor that could be developed is a laser-induced fluorescence sensor. The laser beam would be resonant with a gas Just above the surface of the instrument. The laser would excite fluorescence in the molecule and the fluorescence would be collected by the fiber/lens/DOE. Using the approach, gas concentrations, temperatures, and possibly velocities could be measured. Furthermore, instead of a laser, an electron beam or Terahertz radiation beam could be used as an excitation source. This would be particularly useful in rarefied atmospheres (low pressure) where the beam could propagate and would excite fluorescence in ambient gases such as nitrogen, oxygen, and $CO_2$. The fluorescence would be collected and processed to measure temperature and/or gas concentration. For such sensors, simple intensity measurements alternatively combined with low resolution dispersion provided by a prism or grating would suffice. That is, an Iodine filter, Fabry-Perot etalon, or DWDM would not be required.

It is possible to perform Raman scattering with this device as well, despite the low signal levels usually obtained with Raman scattering. The Rayleigh scattering device described herein would also induce Raman scattering that could be collected by the fibers. Spectral filtering and/or dispersion would be required to observe the collected Raman signal. However, once the spectrum is dispersed and interpreted, the sensor could measure the relative concentrations of $N_2$, $O_2$, $H_2O$, $CO_2$, $H_2$ and $CH_4$ to mention a few species.

This sensor could also be used in a differential absorption LIDAR (DIAL) mode. In this mode two wavelengths are used: one resonant with a gas and the other off resonance. Instead of collecting fluorescence, DIAL uses light collected at the laser's wavelength to measure the attenuation of the resonant beam caused by absorption. The non-resonant beam is also detected to act as a reference. This method would be particularly suitable for measuring water vapor which would be useful in a variety of applications including humidity measurement and scramjet engines. The non-resonant beam could also be used to measure velocity at the same time as described above.

A key difference between this technology and conventional LIDAR is that LIDAR usually uses time-of-flight to get ranging information. In the proposed method, ranging is accomplished by tailoring the use of fibers or diffractive optical elements (DOEs). These fibers or DOEs view specific locations above the surface, providing spatial resolution.

A very similar sensor as described above could be built by using a direct plasma (spark) generation device instead of laser. Two electrodes could either produce a DC plasma or an AC plasma just above the surface of the sensor. The plasma could also be caused by a laser beam projected through the fiber or through free space above the sensor. The plasma would stimulate emission from the gases; this light would be collected and analyzed as described above to detect gas species.

While the invention has been described with reference to specific embodiments thereof, it will be understood that numerous variations, modifications, and additional embodiments are possible and all such variations, modifications, and embodiments are to be regarded as being within the spirit and scope of the invention.

What is claimed is:

1. A light scatter sensor comprising:
    a sensor body in which are positioned a plurality of optical fibers, wherein the sensor body includes a surface and one end of each of the optical fibers terminates at the surface of the sensor body;
    wherein a first optical fiber of the plurality of optical fibers is an illumination fiber for emitting light;
    wherein a plurality of second optical fibers of the plurality of optical fibers are collection fibers for collecting scattered light signals; and
    a light signal processor connected to the plurality of collection fibers and adapted to detect the scattered light signals collected by the collection fibers;
    wherein the sensor is a plasma/spark sensor.

2. A light scatter sensor as described in claim 1, wherein a field of view of the emitted light intersects with a field of view of a first collection fiber, a second collection fiber, and a third collection fiber to form a measurement volume defined by the intersection of the three collection fiber fields of view and the emitted light field of view.

3. A light scatter sensor as described in claim 2, wherein a plurality of measurement volumes is detected by a plurality of sets of at least three collection fibers.

4. A light scatter sensor as described in claim 1, wherein the ends of the collection fibers that terminate at the surface of the sensor body each comprise a lens.

5. A light scatter sensor as described in claim 2, wherein the first, second and third collection fibers are positioned substantially equidistantly around an imaginary circle defined by the ends of the three collection fibers, and the end of the illumination fiber is positioned substantially in the center of the imaginary circle.

6. A light scatter sensor as described in claim 3, wherein each set of at least three collection fibers is positioned substantially equidistantly around an imaginary circle defined by the ends of the three collection fibers, and the end of the illumination fiber is positioned substantially in the center of the imaginary circle; and each set of collection fibers defines a different size circle from the other sets of collection fibers.

* * * * *